United States Patent [19]
Chen et al.

[11] Patent Number: 6,136,884
[45] Date of Patent: Oct. 24, 2000

[54] HAIR CARE COMPOSITIONS

[75] Inventors: Robert Gow-Sheng Chen; Phillip Michael Cook, both of Kingsport, Tenn.

[73] Assignee: Eastman Chemical Company, Kingsport, Tenn.

[21] Appl. No.: 09/016,401

[22] Filed: Jan. 30, 1998

Related U.S. Application Data

[60] Provisional application No. 60/037,082, Feb. 4, 1997.

[51] Int. Cl.[7] ........................................... C08L 51/08
[52] U.S. Cl. .................... 523/105; 523/201; 524/513; 524/603; 524/609; 525/445; 525/902
[58] Field of Search ..................... 524/603, 609, 524/513; 525/445, 902; 523/201, 105

[56] References Cited

U.S. PATENT DOCUMENTS

| | | |
|---|---|---|
| 3,734,874 | 5/1973 | Kibler et al. . |
| 3,779,993 | 12/1973 | Kibler et al. . |
| 4,119,680 | 10/1978 | Vachon . |
| 4,300,580 | 11/1981 | O'Neill et al. . |
| 4,868,051 | 9/1989 | Groejean .................... 428/336 |
| 4,973,656 | 11/1990 | Blount . |
| 4,985,239 | 1/1991 | Yahagi et al. . |
| 5,156,651 | 10/1992 | Girardeau et al. ............. 525/445 |
| 5,158,762 | 10/1992 | Pierce . |
| 5,218,032 | 6/1993 | Sharma .................... 524/513 |
| 5,266,303 | 11/1993 | Myers et al. . |
| 5,441,728 | 8/1995 | Tsaur et al. . |
| 5,660,816 | 8/1997 | Adams et al. . |
| 5,662,893 | 9/1997 | George et al. . |
| 5,674,479 | 10/1997 | George et al. . |
| 5,912,281 | 6/1999 | Clark et al. .................... 524/513 |

FOREIGN PATENT DOCUMENTS

| | | |
|---|---|---|
| 0 705 595 A2 | 10/1995 | European Pat. Off. . |
| 0 687 459 A1 | 12/1995 | European Pat. Off. . |
| 0 705 595 | 4/1996 | European Pat. Off. . |
| 2 719 995 A1 | 11/1995 | France . |
| 1 540 862 | 2/1979 | United Kingdom . |

OTHER PUBLICATIONS

S.I. Um et al, "Morphological Core/Shell Structure and Dispersion Stability of Water–Dispersible Copolyester Graft Polymerized with Acrylic Acid and Ethyl Acrylate," *Journal of Applied Polymer Science*, vol. 60, 1587–1593 (1996).

*Primary Examiner*—Andrew E. C. Merriam
*Attorney, Agent, or Firm*—Matthew W. Smith; Harry J. Gwinnell

[57] ABSTRACT

A latex composition for hair care containing a hybrid-graft copolymer of a sulfopolyester and an acid-functional polymer segment. The acid-functional polymer segment is formed from at least one acid-functional monomer, at least one ethylenically unsaturated monomer, and at least one amide-containing monomer. Such compositions exhibit superior curl retention even at high humidity.

19 Claims, 1 Drawing Sheet

HAIR CARE COMPOSITIONS

This application claims priority of copending provisional application Ser. No. 60/037,082 filed on Feb. 4, 1997 which is incorporated herein by reference.

BACKGROUND OF THE INVENTION

1. Field of the Invention

This invention relates to a hybrid-graft copolymer having a sulfopolyester grafted with an acid-functional polymer. The hybrid-graft copolymer is well-suited for use in hair care formulations. The hybrid-graft copolymer has excellent curl retention, even at high humidity, and may be formulated over a wide range of volatile organic component (VOC) content.

2. Description of the Related Art

A hair care product must meet a variety of requirements. Performance requirements include, for example, exhibiting fine spray pattern, good film formation, good holding power, prolonged curl retention, low stickiness and lack of powdering or flaking, being clear, transparent and glossy and easy to remove upon washing the hair with soap or shampoo. In addition, recent environmental legislation in some states requires hair care products to be formulated with a low content of volatile organic compounds (VOC). Polymer systems addressing at least some of these requirements are disclosed in the following patents:

U.S. Pat. No. 5,441,728 describes a blend of a water-soluble polymer, having a particular viscosity in water, with a latex of water-insoluble polymeric particles dispersed in water of a particular glass transition temperature, The latex and the water-soluble polymer interact with one another to provide a hair setting composition.

U.S. Pat. No. 4,985,239 describes a hair cosmetic composition containing a particulate polymer having an average particle diameter of from 0.005 to 0.2 $\mu$. The particulate polymer is preferably in the form of a polymer latex. The particulate polymer can be blended in hair cosmetic compositions for shampoos, rinses, treatments, hair sprays, set lotions and the like. A conventional emulsion polymerization process cannot be used to prepare the particulate polymer.

U.S. Pat. No. 4,300,580 describes a hair grooming composition containing a linear polyester derived from a dicarboxylic acid, a diol and a difunctional monomer containing a —$SO_3M$ group attached to an aromatic nucleus which is dissipatable in water and water-alcohol mixtures. The diol component of the polyester contains at least 20 mol % of a poly(ethylene glycol). Such formulations are fast drying and have good hair holding properties, but possess the disadvantage of being very difficult to remove from the hair.

U.S. Pat. No. 5,266,303 describes aerosol hair spray formulations based on a sulfonate-containing, water-dispersible or water-dissipatable linear polyester having a glass transition temperature of about 36° C. to about 40° C., a water-soluble polyvinyl lactam polymer, and water.

U.S. Pat. No. 5,158,762 describes a water-based hair spray composition capable of providing a fine finishing mist which provides a stiff resin film having excellent hair holding power, with superior shine, and feel, and within a relatively low drying time, approaching that of alcohol-based systems. The composition attains its attributes by including a predetermined blend of at least two hair spray resins, one being a water-soluble resin, and the other resin being a water-dispersible polyester or polyester amide.

EP Application No. 2 719 995 describes an aqueous cosmetic composition for hair setting based on the combination in an aqueous or low alcohol medium of a sulfonated polycondensation water dispersible group and a water-soluble copolymer containing one neutralized carboxylic acid group and by patterns including a cyclic ester group. The composition has excellent setting power and can be satisfactorily washed away with shampoo.

EP Application No. 0 687 459 A1 describes capillary compositions containing an aqueous dispersion of polymers, such as polyesters, polyamides or alkyds, as film forming agents. The polymers are prepared by radical polymerization of a radical monomer inside and/or partially on the surface of the preexisting particles of the polymer.

EP Application No. 0 705 595 A2 describes aqueous low VOC hair styling compositions containing at least one acrylic hair fixative resin and one or more plasticizing compounds selected from polycarboxylic acid esters and dimethiconecopolyols. Also described are low beading, low VOC hair styling compositions containing at least one surface tension reducing compound, at least one acrylic hair fixative resin, and at least one simethicone. Aqueous hair resin compositions containing at least one acrylic hair fixative resin and iodopropynyl-butylcarbamate are also described. An acrylic hair fixative resin contains an alkyl (meth)acrylate monomer, a hydroxyalkyl (meth)acrylate monomer, and a monoethylenically unsaturated monocarboxylic acid monomer.

Despite such efforts, there still exists a need for a hair care polymer composition which is compatible with a wide range of VOC and able to form suitable formulations at a broad range of solvent concentrations. In addition, there is a need for a hair fixing composition which exhibits superior curl retention, even at high humidity levels.

SUMMARY OF THE INVENTION

The invention fulfills these needs by providing latex compositions for hair care containing a hybrid-graft copolymer of a sulfopolyester and an acid-functional polymer. Such a hybrid-graft copolymer demonstrates excellent curl retention, even at high humidity.

The invention also provides hair care formulations containing a hybrid-graft copolymer of a sulfopolyester and an acid-functional polymer. Such formulations are compatible with volatile organic compounds and may be prepared over a wide range of volatile organic compound (VOC) concentrations.

The invention further provides methods for the preparation of a hybrid-graft copolymer of a sulfopolyester and an acid-functional polymer.

DETAILED DESCRIPTION OF THE INVENTION

Figure 1:
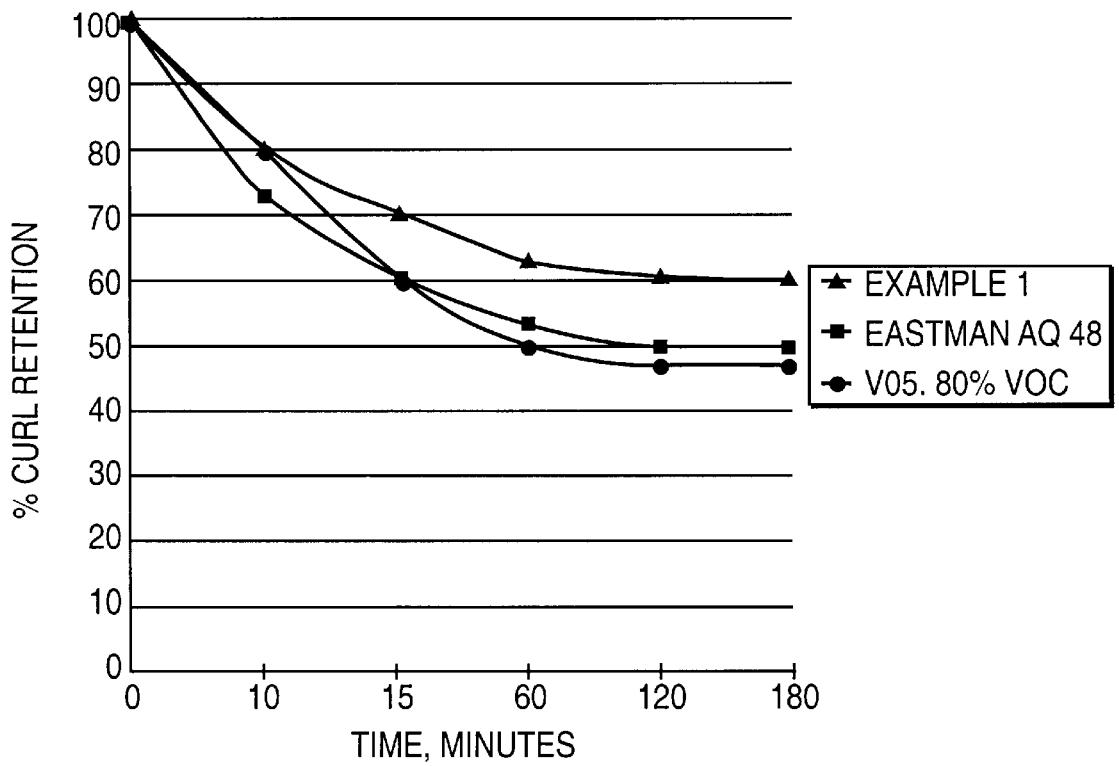
FIG. 1 depicts curl retention properties of hybrid-graft emulsion polymers and of commercially available materials at 72+ F. and 90% relative humidity (RH) as a function of time.

The invention provides a latex composition containing a hybrid-graft copolymer. The composition is useful in hair care formulations, particularly in both aerosol and pump hair spray formulations. The hybrid-graft copolymer contains a sulfopolyester grafted with an acid-functional polymer segment. The term "hybrid" denotes that the graft copolymer may contain not only a sulfopolyester grafted with an acid-functional polymer segment (sulfopolyester-g-acid-functional polymer), but in addition may contain small amounts of free sulfopolyester and free acid-functional polymer. The graft yield on a polyester depends on the acid content of graft monomers, as discussed in S.I. Um et al, "Morphological Core/Shell Structure and Dispersion Stability of Water-Dispersible Copolyester Graft Polymerized with Acrylic Acid and Ethyl Acrylate," *Journal of Applied Polymer Science,* Vol 60, 1587–1593 (1996).

The hybrid-graft copolymer contains a sulfopolyester in an amount of from about 2 to about 90 wt % and a grafted acid-functional polymer segment in an amount of from about 10 to about 98 wt % based on the total dry weight of the hybrid-graft copolymer. A preferred hybrid-graft copolymer of the invention contains about 10 to about 80 wt % of the sulfopolyester and about 20 to about 90 wt % of the acid-functional polymer segment based on the total dry weight of the hybrid-graft copolymer. A more preferred hybrid-graft copolymer contains about 20 to about 70 wt % of the sulfopolyester and about 30 to about 80 wt % of the acid-functional polymer segment based on the total dry weight of the hybrid-graft copolymer.

The hybrid-graft copolymer preferably has a weight average molecular weight (Mw) from about 15,000 to about 250,000, more preferably from about 20,000 to about 200,000, as measured by gel permeation chromatography (GPC). The hybrid-graft copolymer preferably has a glass transition temperature (Tg) ranging from about 15 to about 130° C., and most preferably from about 25 to about 55° C. The sulfopolyester and acid-functional polymer segment of the hybrid-graft copolymer are discussed in more detail below.

The Sulfopolyester

A sulfopolyester, useful in the present invention, may be any polyester having sulfonate groups such as those described in U.S. Pat. Nos. 3,734,874, 3,779,993, 4,119,680, 4,300,580, 4,973,656, 5,660,816, 5,662,893, and 5,674,479 each of which is incorporated herein by reference. Preferably, the sulfopolyester exhibits a glass transition temperature (Tg) in the range of 15–60° C. Further, the sulfopolyester has a preferred weight average molecular weight (Mw) of from about 4,000 to about 20,000, as determined by gel permeation chromatography (GPC). Preferably, a sulfopolyester used in the invention forms a hard clear film at room temperature. A preferred sulfopolyester is, for example, the EASTMAN AQ®-48 polyester product available from Eastman Chemical Company, Kingsport, Tenn.

The sulfopolyester may be synthesized by techniques known in the art. Various methods to prepare a sulfopolyester are described in U.S. Pat. Nos. 3,734,874 and 3,779,993. In general, a preferred sulfopolyester may be formed by condensation polymerization of about 15 to about 26 mol % dimethyl-5-sodiosulfoisophthalate and about 60 to about 80 mol % isophthalic acid based on 100 mol % dicarboxylic acid, about 10 to about 30 mol % of 1,4-cyclohexanedimethanol and about 70 to about 90 mol % diethylene glycol based on 100 mol % of diol.

The Acid-functional Polymer Segment

An acid-functional polymer segment, in accordance with the present invention, is a polymer or copolymer of ethylenically unsaturated monomers at least one of which contains acid functionality such as, for example, carboxyl or sulfonic acid groups. Partial or complete neutralization of the acid functionality renders the hybrid-graft copolymer dispersible or soluble in water or a liquid vehicle containing water, such as those used in hair care formulations. The acid-functional polymer segment of the hybrid-graft copolymer contains the following components: (1) an acid-functional monomer, (2) an ethylenically unsaturated monomer, and (3) an amide-containing monomer. Generally, the acid-functional polymer segment contains: about 15 to about 50 wt % of an acid-functional monomer, (2) about 10 to about 80 wt % of an ethylenically unsaturated monomer, and (3) up to about 40 wt % of an amide-containing monomer. The weight percentages of these monomers are based on the total weight of the polymer segment. These and other components of the acid-functional polymer segment are discussed below.

Acid-functional Monomers

An acid-functional monomer, in accordance with the present invention, is a monomer containing an acid functionality, such as a carboxylic acid group, a sulfonic acid group, an acid anhydride, or other group which can react with a base to form a salt. Suitable acid-functional monomers in accordance with the invention include, but are not limited to, acrylic acid, methacrylic acid, itaconic acid, itaconic anhydride, citraconic acid, maleic acid, fumaric acid, crotonic acid, maleic anhydride, citraconic anhydride, vinyl sulfonic acid, 2-acrylamido-2-methyl propane sulfonic acid, and styrene sulfonic acid. Mixtures of such acid-functional monomers may also be used. Of these, methacrylic acid, itaconic acid and acrylic acid represent preferred monomers.

The acid-functional polymer segment may generally contain about 15 to about 50 wt % of an acid-functional monomer based on the total weight of the acid-functional polymer segment. Preferably, the acid-functional monomer is present in an amount ranging from about 20 to about 50 wt % based on the total weight of the acid-functional polymer segment. A more preferred range is from about 25 to about 40 wt %, based on the total weight of the acid-functional polymer segment. The amount of the acid-functional monomer may be varied so that when partially or fully neutralized, the hybrid-graft copolymer will disperse or be soluble in water or in a mixture of water and at least one alcohol, ketone, or lower alkyl ester.

Ethylenically Unsaturated Monomers

The acid-functional polymer segment may contain an ethylenically unsaturated monomer in amounts ranging from about 10 to about 80 wt %, based on the acid-functional polymer segment. More preferably the ethylenically unsaturated monomers are present in about 20 to about 60 wt %.

One type of ethylenically unsaturated monomers useful in the invention are α,β-ethylenically unsaturated monomers having the general formula:

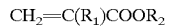

$$CH_2=C(R_1)COOR_2$$

For monomers of this general formula, $R_1$ is hydrogen or a $C_1$–$C_3$ alkyl group. $R_2$ is a $C_1$–$C_{20}$ alkyl group, phenyl, benzyl, hydroxy-($C_1$–$C_4$)-alkyl, $C_1$–$C_4$ alkoxy-($C_1$–$C_4$) alkyl, cyclopentyl, cyclohexyl, furyl, $C_1$–$C_4$ alkyl furyl, tetrahydrofuryl or a $C_1$–$C_4$ alkyl tetrahydrofuryl, or combinations of these monomers. Combinations of monomers where $R_1$ is hydrogen and monomers where $R_1$ is an alkyl group are used to modify the hydrophobicity and the glass transition temperature (Tg) of the film of the hybrid-graft copolymer.

Examples of suitable ethylenically unsaturated monomers of the above formula, include, but are not limited to, methyl (meth)acrylate, ethyl (meth)acrylate, butyl (meth)acrylate, hexyl (meth)acrylate, isooctyl (meth)acrylate, isodecyl (meth)acrylate, lauryl (meth)acrylate, stearyl (meth) acrylate, phenoxyethyl (meth)acrylate, methoxyethyl (meth) acrylate, benzyl (meth)acrylate, furyl (meth)acrylate, methylfuryl (meth)acrylate, butylfuryl (meth)acrylate, tetrahydrofuryl (meth)acrylate, ethoxyethyl (meth)acrylate, 2-ethylhexyl (meth)acrylate, cyclopentyl (meth)acrylate, isobornyl (meth)acrylate, hydroxyethyl (meth)acrylate, hydroxypropyl (meth)acrylate and combinations or mixtures thereof. Among these, preferred monomers are methyl (meth)acrylate, ethyl (meth)acrylate, butyl (meth)acrylate, 2-ethylhexyl (meth)acrylate, 2-hydroxyethyl (meth)acrylate and mixtures thereof. The term "(meth)acrylate" is used here and throughout the specification to denote methacrylate and acrylate monomers.

Other ethylenically unsaturated monomers which may be used in the acid-functional polymer segment include styrene derivatives and vinyl derivatives. Examples of suitable styrene derivatives include, but are not limited to, styrene, a-methyl styrene, p-methyl styrene, and m-methyl styrene. Vinyl derivatives include, but are not limited to, vinyl esters such as, for example, vinyl acetate, vinyl propionate, vinyl 2-ethylhexanoate, vinyl neononanoate, and vinyl neodecanoate.

One or more wet adhesion promoting ethylenically unsaturated monomers may also be used in the acid-functional polymer segment to enhance hair substantivity. Examples of wet adhesion promoting monomers include t-butylaminoethyl methacrylate, dimethylaminoethyl methacrylate, diethylaminoethyl methacrylate, N,N-dimethylaminopropyl methacrylate, 2-t-butylaminoethyl methacrylate, N,N-dimethylaminoethyl acrylate, and N-(2-methacryloxyethyl) ethylene urea.

Amide-containing Monomer

An amide-containing monomer may be incorporated into the acid-functional polymer segment to enhance hair substantivity and/or the hair affinity of the hybrid-graft copolymer. Examples of such amide-containing monomers include, but are not limited to, vinyl pyrrolidone or N-substituted acrylamides. Exemplary N-substituted acrylamides are N-ethyl (meth)acrylamide, N-t-butyl (meth)acrylamide, N-t-octyl (meth)acrylamide, N-decyl (meth)acrylamide, N-dodecyl (meth)acrylamide, ethylphenyl (meth) acrylamide, and butylphenyl (meth)acrylamide. Mixtures of amide-containing monomers may also be used. The preferred amide-containing monomers are N-t-butyl acrylamide and N-octyl acrylamide. The amide-containing monomer may be present in an amount of up to about 40 wt %, based on the total weight of the acid-functional polymer. The preferred range for the amide-containing monomer is between about 4 to about 25 wt %, based on the total amount of the acid-functional polymer.

Preparation of the Hybrid-graft Copolymer

The hybrid-graft copolymer of the invention may be synthesized by emulsion polymerization of the monomers making up the acid-functional segment polymer in the presence of an aqueous dispersion of the sulfopolyester, each as described above. The hybrid-graft copolymer of the invention may be prepared using conventional emulsion polymerization techniques. For example, a batch process or a semi-continuous process may be used to prepare the hybrid-graft copolymer. A semi-continuous process is preferred.

In a preferred semi-continuous process, a solution or dispersion of a sulfopolyester in water is prepared containing about 5 to about 40 wt % of a sulfopolyester based on the total weight of the solution. A mixture of one or more monomers to form an acid-functional polymer segment and a polymerization initiator may then be gradually added to the aqueous dispersion of the sulfopolyester. Polymerization then produces an aqueous hybrid-graft dispersion. It is generally desirable to have less than 100 parts per million (ppm) of residual monomers in the final product and preferably less than 50 ppm residual monomer(s). The aqueous dispersion thus produced may be prepared with a total solids content from about 20% to about 60 wt %, based on the total aqueous dispersion. It is generally preferred, for safety reasons, not to mix the initiator with the monomers but to add the initiator and the monomers as separate components, although concurrently, to the aqueous dispersion of the sulfopolyester.

The reaction temperature of the emulsion graft-polymerization is generally determined by the type of initiator. Accordingly, the reaction temperature may range between about 30° C. to about 90° C., with a preferred reaction temperature being between about 60° and about 85° C. Typical initiators known in the art may be used to prepare the hybrid-graft copolymer of the present invention. Such initiators include, but are not limited to, peroxygen or persulfate compounds such as, for example, hydrogen peroxide, sodium persulfate, potassium persulfate or ammonium persulfate, t-butyl hydroperoxide, cumene hydroperoxide, lauryl peroxide, and benzoyl peroxide. A preferred amount of a peroxygen or persulfate initiator in accordance with the invention is between about 0.05 and about 1.5 wt %, based on the total weight of the monomers. Redox initiators may also be used. Such redox initiators include, but are not limited to, combinations of peroxygen compounds with sodium formaldehyde sulfoxylate, ascorbic acid (e.g. isoascorbic acid), glyoxal bisulfite, or divalent iron salts. The preferred amount of a redox initiator is about 0.02–1.5 wt %, based on the total weight of the monomer content.

In an emulsion polymerization to prepare the hybrid-graft copolymer, an emulsifying agent may also be used, as known in the art. Examples of emulsifying agents are, but not limited to, a fatty acid, alkyl sulfate, alkyl sulfonate, alkylarylsulfonate, sulfated polyethoxylated alkyl phenol, sulfo succinate, alkali-metal alkyl phosphate, salt of abietic acid (hydrogenated or non-hydrogenated), and non-ionic emulsifiers, such as polyoxylated fatty alcohol, polyethoxylated alkyl phenol, and polyethoxylated fatty acid. An emulsifying agent may typically be used in an amount up to about 4 wt %, based on the total weight of the monomers.

A chain transfer agent may also be employed, if desired, to regulate the molecular weight of the hybrid-graft copolymer. Examples of chain transfer agents are, but not limited to, mercaptans, such as dodecylmercaptan, t-butyl mercaptan, and 2-ethylhexyl-3-mercapto propionate, and haloalkyl compounds such as carbon tetrabromide and bromodichloromethane.

The invention also provides a hybrid-graft copolymer having different acid-functional polymer segments grafted on the sulfopolyester. Such a hybrid-graft copolymer may, for example, contain about 5 to about 80 wt % of a sulfopolyester, from about 15 to about 55 wt % of a first acid-functional polymer segment, and about 5 to about 40 wt % of a second acid-functional polymer segment, based on the total hybrid-graft copolymer weight. The first and second acid-functional polymer segments preferably have different compositions and glass transition temperatures (Tg).

A hybrid-graft copolymer having different acid-functional polymer segments grafted onto the sulfopolyester, according to the present invention, may be prepared by sequential emulsion polymerization. For example, in a semi-continuous process a dispersion of a sulfopolyester in water is prepared. Subsequently, a mixture of one or more monomers to form a first acid-functional polymer segment is gradually added to the reactor under the polymerization conditions as described above. Sequentially, another mixture of one or more monomers to form a second acid-functional polymer segment is added to the reactor. Accordingly, the polymer segments may be prepared from different monomer mixtures and have different glass transition temperatures. The term glass transition temperature (Tg) refers to the Tg of the polymer derived from the polymerization of the monomer mixture. Preferably, the Tg of a first acid-functional polymer segment is higher than the Tg of a second acid-functional polymer segment or other segments. It is further preferred that the Tg of a first acid-functional polymer mixture is between about 40 and about 80° C., while the Tg of a second acid-functional polymer is between about 20 and about 50° C.

The hybrid-graft copolymer is substantially insoluble in water or a liquid vehicle containing water at a low pH (below about 6.0). However, when the pH is adjusted to a value of from about 6.0 to about 9.5, the hybrid-graft copolymer exhibits substantial dissolution in aqueous media. Preferably, the pH ranges from about 6.5 to about 8.0. Solubilization or dispersion of the hybrid-graft copolymer may be accomplished by neutralizing (or reacting) at least some or all of the acid functionalities of the acid-functional polymer segment of the hybrid-graft copolymer with a Brönsted base. Examples of inorganic Brönsted bases include, but are not limited to, sodium hydroxide, potassium hydroxide, ammonium hydroxide, ammonium carbonate or combinations thereof. Organic bases may also be used and includes for example, water-soluble bases such as monoethanolamine (MEA), diethanolamine (DEA), triethanolamine (TEA), 2-methyl-2-amino-1-propanol (AMP), 2-amino-2-methyl propanediol, N,N-dimethyl-2-amino-2-methyl-1-propanol, monoisopropanolamine, triisopropanolamine, morpholine, monoamine glycols, and the like.

The degree of neutralization required for solubilization varies for each graft copolymer. The final pH of the solution preferably ranges from about 6.0 to about 9.5, and more preferably from about 6.5 to about 8.0. A buffer may be used to maintain a desired pH. The lowest neutralization level needed to render the polymer water soluble or dispersible depends on the type of polymer, the amount of water and the amount and type of the VOC in the hair care formulation.

The use of more hydrophilic monomers in the acid-functional polymer segment may also enhance aqueous solubility of the hybrid-graft copolymer. Thus, the hydrophobicity/hydrophilicity of the ethylenically unsaturated monomers for the acid-functional polymer segment may be adjusted so that the hybrid-graft copolymer may be more or less dispersible or soluble in water or a liquid vehicle containing water at a particular pH.

The hybrid-graft copolymer may be isolated from the aqueous dispersion in a powder form by techniques known in the art. The powder material may be obtained by any of the conventional methods such as spray drying, coagulation-filtration-drying, freeze drying, and the like. The dried powder may be re-dispersed in water, using an alkaline base, preferably a volatile amine or ammonia.

Hair Care Formulations

In another embodiment, the invention provides a hair care formulation containing: (I) a hybrid-graft copolymer, according to the invention, (II) a liquid vehicle and (III) at least one volatile organic compound. Generally, a hair care formulation of the invention contains: (I) from about 0.5 to about 20 wt % of a hybrid-graft copolymer on a dry basis, according to the invention, (II) from about 80 to about 99.5 wt % of a liquid vehicle and (III) up to about 80 wt %, of at least one volatile organic compound. The weight percentages are based on the total weight of the hair care formulation. In a preferred embodiment, the hybrid-graft copolymer on a dry basis is present in an amount of from about 0.5 to about 15 wt %, preferably about 3 to about 10 wt %, and more preferably about 4 to about 8 wt %, based on the total weight of the hair care formulation.

A hair care formulation of the invention may be formulated as an aerosol hair spray, pump hair spray, styling gel, spray-on gel, or mousse. The hybrid-graft copolymer of the invention has been found to be exceptionally useful in such formulations, particularly in aerosol hair spray formulations and pump hair spray formulations. Hair care formulations of the invention exhibit, quite unexpectedly, superior hair form retention, such as curl retention, even at high humidity over commercial sulfopolyester-containing hair fixation products. The hair care formulations of the invention form a glassy and clear film and may be easily washed out from hair by shampooing. The films produced from the formulation exhibit low water absorption even at high humidity, and as a result the hair does not stick together and the hairstyle is not lost. Although the film-forming formulations of this invention are particularly useful as hair care formulations to groom hair, it is possible that the formulations, with or without modification, may be used in other types of personal care products.

A liquid vehicle of a hair care formulation of the invention may be water or an aqueous system such as a mixture of water and at least one alcohol, ketone, or lower alkyl ester. If a mixture of water and at least one alcohol, ketone, or lower alkyl ester is used, the amount of volatile organic components which include the alcohol and/or ketone and/or lower alkyl ester and, in the case of an aerosol formulation, the propellant, should generally not exceed about 80 wt % of the liquid vehicle, and preferably should not exceed about 60 wt % of the liquid vehicle of the hair care formulation. Therefore, at least about 20 wt % and preferably about 40 wt % of the liquid vehicle is water. Furthermore, if an alcohol/water mixture is used, the alcohol is present preferably in an amount of about 10 to about 30 wt % based on the weight of the hair spray formulation. If a ketone/water mixture is used, the ketone is present preferably in an amount of about 10 to about 30 wt % based on the weight of the hair care formulation. If an alcohol/ketone/water mixture is used, the alcohol is present preferably in an amount of about 5 to about 25 wt % and the ketone is present preferably in an amount of about 5 to about 25 wt % based on the weight of the hair care formulation. A liquid vehicle containing alcohol and/or ketone provides faster drying of the formulation on hair as compared to formulations prepared with only water. The alcohol may be an aliphatic straight or branched chain having 2 to 4 carbon atoms. Ethanol, propanol, and isopropyl alcohol are the preferred alcohols. The ketone may be an aliphatic straight chain ketone having 3 to 5 carbon atoms. Acetone and 2-butanone are the preferred ketones. A lower alkyl ester may also be used in a liquid vehicle. Preferably, the lower alkyl ester is an acetate ester, more preferably, methyl or ethyl acetate.

Volatile organic compounds (VOCs) represent an optional third component of a hair care formulation of the invention. According to the invention, a hair care formulation may contain zero volatile organic compounds (VOCs) or up to a level of about 80 wt % VOC, based on the total weight of the formulation. Zero-VOC clear solutions may be prepared by partially neutralizing a latex composition of the invention as described above. Solutions or formulations having zero-VOC are suitable for zero-VOC pump, lotion, or gel formulations. Suitable VOCs for VOC-containing formulations include, for example, $C_1$–$C_{12}$ straight or branched chain alcohols. Preferred alcohols include, for example, methanol, ethanol, propanol, isopropanol, butanol and t-butanol. In addition, other preferred VOCs include $C_1$–$C_{12}$ straight or branched chain hydrocarbons such as methane, ethane, propane, isopropane, isobutane, pentane, isopentane, and butane are also suitable VOCs. Further preferred VOCs include ethers such as dimethyl ether, diethyl ether and dimethoxy methane.

A hair spray formulation of the invention may also contain conventional hair care adjuvants known in the art in amounts which generally range up to about 20%, preferably from about 0.01% to about 10% by weight based on the total weight of the hair care formulation. Examples of adjuvants include, but are not limited to, plasticizers, coalescing agents, silicones, emollients, emulsifiers, lubricants and penetrants such as various lanolin compounds, protein hydrolysates, or other protein derivatives, thickness and viscosity modifiers, ethylene adducts and polyoxyethylene cholesterol, dyes, tints and other colorants, perfumes or fragrances, preservatives, antifoaming agents, chelating agents, polymers and resins, hair conditioners, pH adjusting agents, and the like. Some of these conventional adjuvants are discussed below.

A plasticizer or a coalescing agent may be added to modify the film forming characteristics of a hair care formulation of the invention. Examples of plasticizers include, but are not limited to, glycols, adipic esters, phthalate esters, isobutyrate esters, terephthalate esters, epoxidized butyl esters or fatty acids, epoxidized vegetable oils, glycerine as well as polymeric plasticizers. More preferred plasticizers in accordance with the invention are, for example, di-2-ethylhexyladipate or dioctyladipate (DOA), di-2-ethylhexyl phthalate or dioctyl phthalate (DOP), di-2-ethylhexyl terephthalate (DOTP), dicyclohexyl phthalate, diisononyl adipate, diisononylphthalate, n-butyl benzyl phthalate, 1,3-butylene glycol/adipic acid polyester, dialkyl adipate, dialkyl phthalate derivatives where the alkyl group is a $C_1$–$C_{12}$ alkyl group, or preferably a $C_7$, $C_9$ or $C_{12}$ alkyl group, di-n-hexylazelate, diphenylphthalate, tricresol phosphate, benzyl benzoate, dibutyl phosphate, tributyl phosphate, tributoxyethyl phosphate, triphenyl phosphate, butyl acetyl ricinoleate, glycerol acetyl ricinoleate, dibutyl phthalate, diethyl phthalate, dioctyl phthalate, dimethoxyethyl phthalate, diisobutyl phthalate, diamyl phthalate, dibutyl glycolate, butyl stearate, triethyl citrate, tributyl citrate, tributyl acetyl citrate, 2-hexyltriethylacetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3-pentanediol diisobutyrate (TXIB), methyl abietate, cumyl acetate, dibutoxyethyl adipate, di-n-hexylazalate, glyceryl-tri-benzerate, tri-n-butylcitrate, dioctyl fumarate, triisonyl trimellitate, dioctyl isophthalate, butyl oleate, chlorinated paraffin, tricresolphosphate and dibutyl sebacate. Other plasticizers include: Dimethicone copolyol (Dow Corning 190) at 0.01–0.02%, PEG-6 capric/caprylic glyceride (SOFTIGEN 767) at 0.5–2%, DIACETIN at 1–2%, LAURAMIDE DEA (MONAMID 716) at 0.1–1%, Phenyl trimethicone (ABIL AV 20-1000) at 0.1–0.2%, propylene glycol at 1–5%, and dipropylene glycol at 1 to 5%. Examples of coalescing solvents include, but are not limited to, acetone, methyl acetate, di- or tri-propylene glycol methyl ethers.

A hair care formulation of the invention may contain other polymers or resins typically used in hair care formulations. Such polymers or resins may be present in an amount of up to about 50 wt %, based on the amount of total polymer present, preferably, in an amount of about 0.5 to about 20 wt %. Such polymers or resins are homopolymers or copolymers that may be rendered dispersible or soluble in water or in a liquid vehicle containing water such as, for example, alcohol/water, or alcohol/ketone/water mixtures. Examples of these polymers or resins include, but are not limited to, the mono ethyl, isopropyl, or n-butyl esters of poly(methyl vinyl ether/maleic acid), poly-N-vinyl pyrrolidone, poly (N-vinyl pyrrolidone/vinyl acetate), poly (N-vinyl pyrrolidone/ethyl (PVP), copolymers of PVP and methyl methacrylate, methacrylate/methacrylic acid), poly (ethyl acrylate/acrylic acid/N-tert-butyl acrylamide), PVP/ethyl methacrylate/methacrylic acid terpolymer poly (vinyl acetate/crotonic acid), polyvinyl alcohol (PVA), copolymers of PVA and crotonic acid, copolymers of PVA and maleic anhydride, hydroxypropyl cellulose, hydroxypropyl methylcellulose, hydroxypropyl guar gum, sodium polystyrene sulfonate, octylacrylamide/acrylate/butylaminoethyl methacrylate copolymers, and mixtures of such polymers or resins.

A hair care formulation of the invention may also include a conditioner in amounts up to about 10 wt %, preferably from about 0.01 wt % to about 10 wt %, and more preferably from about 0.1 wt % to about 5 wt %, based on the total weight of the hair care formulation. Typical conditioners include, for example, a non-volatile silicon compound or a mixture of a low molecular weight polydimethylsiloxane fluid and a higher molecular weight polydimethylsiloxane gum. The non-volatile polydimethylsiloxane mixture may be added to a hair care formulation of the invention in an amount sufficient to provide improved combing and improved feel (softness) to the hair after shampooing.

Another particularly suitable conditioning agent which may be included in a hair care formulation of the invention is a volatile hydrocarbon, such as a hydrocarbon including from about 10 to about 30 carbon atoms. Preferably such a hydrocarbon should have sufficient volatility to slowly volatilize from the hair after application of the hair spray formulation. The volatile hydrocarbons provide essentially the same benefits as the silicone conditioning agents. A volatile hydrocarbon may be used in the formulations of the invention either alone, in combination with another volatile hydrocarbon or silicone. The preferred volatile hydrocarbons are aliphatic hydrocarbons having from about 12 to about 24 carbon atoms and having a boiling point in the range of from about 100° C. to about 300° C. Exemplary volatile hydrocarbons are depicted in general structural formula (I) below, wherein n is an integer ranging from 2 to 5,

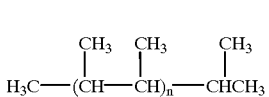

(I)

Examples of commercially-available volatile hydrocarbons useful in a hair spray formulation are PERMETHYL 99A and PERMETHYL 101A products, which correspond to compounds of general structure where n is 2 and 3, respectively. The products are available from Permethyl Corporation, Frazer, Pa.

Water-insoluble conditioning agents may also be incorporated into a hair spray formulation of the invention. These agents include, for example, polysiloxane polyether copolymers, polysiloxane polydimethyl dimethylammonium acetate copolymers, acetylated lanolin alcohols, lauryl dimethylamine oxide, a lanolin-derived extract of sterol ester, lanolin alcohol concentrate, an isopropyl ester of lanolin fatty acid, sulfur rich amino acid concentrate, isopropyl ester of lanolin fatty acid, oleyl alcohol, stearyl alcohol, stearamidopropyl dimethyl myristyl acetate, a polyol fatty acid, a fatty amido amine, guar hydroxypropyltrimethyl ammonium chloride, cetyl/stearyl alcohol, keratin protein derivatives, isostearamidopropyl dimethylamine, stearamidopropyl dimethylamine, an amino functional silicone, isopropyl ester of lanolic acid, ethoxylated (30) castor oil, acetylated lanolin alcohol, fatty alcohol fraction of lanolin, a mineral oil and lanolin alcohol mixture, high molecular weight ester of lanolin, N-vinylpyrrolidone/dimethylaminoethyl methacrylate copolymer, 5 mole % ethylene oxide adduct of soya sterol, 10 mole ethylene oxide adduct of soya sterol, stearic acid ester of ethoxylated (20 mole) methyl glucoside, sodium salt of polyhydroxycarboxylic acid, hydroxylated lanolin, cocamidopropyl dimethylamine lactate, cocamidopropyl dimethylamine propionate, cocamidopropyl morpholine lactate, isostearamidopropyl dimethylamine lactate, isostearamidopropyl morpholine lactate, oleamidopropyl dimethylamine lactate, linoleamidopropyl dimethylamine lactate, a stearamidopropyl dimethylamine lactate, ethylene glycol monostearate and propylene glycol mixture, stearamidopropyl dimethylamine lactate, acetamide monoethanolamine, lactamide monoethanolamine, stearamide monoethanolamine, behenalkonium chloride, a behenyl trimethyl ammonium methosulfate and cetearyl alcohol mixture, cetearyl alcohol, tallow imidazaolinum methosulfate, mixed ethoxylated and propoxylated long chain alcohols, stearamidopropyl dimethylamine lactate, oleamine oxide, stearamide oxide, soya ethyldiammonium ethosulfate, ricinolamidopropyl ethyldimonium ethosulfate, N-(3-isostearamidopropyl)-N, N-dimethyl amino glycolate, N-(3-isostearamidopropyl)-N, N-dimethyl amino gluconate, hydrolyzed animal keratin, ethyl hydrolyzed animal keratin, stearamidoethyl diethylamine, cocamidopropyl dimethylamine, lauramidopropyl dimethylamine, oleamidopropyl dimethylamine, palmitamidopropyl dimethylamine, stearamidopropyl dimethylamine lactate, avocado oil, sweet almond oil, grape seed oil, jojoba oil, apricot kernel oil, sesame oil, safflower oil, wheat germ oil, cocamidoamine lactate, ricinoleamido amine lactate, stearamido amine lactate, stearamido morpholine lactate, isostearamido amine lactate, isostearamido morpholine lactate, wheat germamido dimethylamine lactate, wheat germamidopropyl dimethylamine oxide, disodium isostearamido monoethanolamine sulfo succinate, disodium oleamide PEG-2 sulfo succinate, disodium oleamide monoethanolamine sulfo succinate, disodium ricinoleyl monoethanolamine sulfo succinate, disodium wheat germamido monoethanolamine sulfo succinate, disodium wheat germamido PEG-2 sulfo succinate, stearamido amine, stearamido morpholine, isostearamido amine, isostearamido morpholine, polyethylene glycol (400 moles) and distearates, synthetic calcium silicate, isostearic alkanolamide, ethyl ester of hydrolyzed animal protein, blend of cetyl and stearyl alcohol with ethoxylated cetyl or stearyl alcohol, amido amines, polyamido amine, propoxylated (1-20 moles) lanolin alcohol, isostearamide diethanolamine, and hydrolyzed collagen protein.

A hair care formulation of the invention may also contain other adjuvants to render such formulations more acceptable for use in hair care. For example, emulsifiers include, but are not limited to, cetyl trimethyl ammonium chloride, stearyl dimethyl benzyl ammonium chloride, partially-hydrogenated tallow, and dimethylammonium chloride. Preservatives such as benzyl alcohol, methyl paraben, propyl paraben and imidazolidinylurea may also be used. Thickeners and viscosity modifiers which may be used include, diethanolamide of a long chain fatty acid, and fatty alcohols (for example, cetearyl alcohol), sodium chloride, sodium sulfate, and ethyl alcohol. The pH of a hair care formulation may be adjusted using pH adjusting agents such as citric acid, succinic acid, sodium hydroxide, and triethanolamine. Colorants for use in hair care formulation are, for example, any of the Food, Drug and Cosmetics (FD&C) or Drug and Cosmetics (D&C) dyes. Hair oxidizing (bleaching) agents such as hydrogen peroxide, perborate salts, persulfate salts, and percarbonate salts may also be used. Hair reducing agents such as thioglycolates, represents another type of adjuvant. Perfume oils are also commonly found in hair care products and may be used here. Chelating agents, such as ethylenediamine tetraacetic acid (EDTA), may also be used. These adjuvants are generally used individually at levels of up to about 20%, preferably from about 0.001% to about 20%, more preferably from about 0.01% to about 5% by weight of the total hair care formulation.

Modes of delivery of the above-described hybrid-graft copolymer for aqueous styling aid formulations include, for example, aerosol sprayers, all forms of bag-in-can devices, in situ carbon dioxide generator systems, compressors, and the like. When the hair care formulation is an aerosol hair spray formulation, the formulation also contains a propellant. The propellant may be any liquefiable gas conventionally used for aerosols. Examples of materials that are suitable for use as propellants are, for example, trichlorofluoromethane, chlorodifluoromethane, 1,1-difluoroethane, dichlorotetrafluoroethane, monochlorodifluoromethane, trichlorotrifluoroethane, dimethyl ether, $C_1$–$C_4$ hydrocarbons such as methane, ethane, propane, n-butane, and isobutane, and mixtures thereof. Water-soluble gases such as, for example, dimethyl ether, carbon dioxide, and/or nitrous oxide also may be used to obtain aerosols having reduced flammability. Other insoluble, compressed gases such as, for example, nitrogen, helium, and fully-fluorinated oxetanes and oxepanes also are useful for the aerosol delivery of formulations of the invention.

Preferably, the propellant is either a $C_1$–$C_4$ aliphatic hydrocarbon, 1,1-difluoroethane, or dimethyl ether. A preferred aliphatic hydrocarbon propellant is a mixture containing about 80 to about 85 wt % isobutane and about 15 to about 20 wt % propane. The amount of the propellant is governed by normal factors well-known in the aerosol art. The level of propellant is generally from about 3 wt % to about 60 wt %, preferably from about 5 to about 45 wt %, of the aerosol hair spray formulation. In the case where a $C_1$–$C_4$ aliphatic hydrocarbon is used as the propellant, generally about 3 to about 10 wt % is employed. In the cases where dimethyl ether or 1,1-difluoroethane are used as the propellant, generally, about 20 to about 40 wt % is employed. If a propellant such as dimethyl ether utilizes a vapor pressure suppressant (for example, trichloroethane or dichloromethane), for weight percentage calculations, the amount of suppressant is included as part of the propellant.

The following examples are given to illustrate the invention. It should be understood, however, that the invention is not to be limited to the specific conditions or details set forth in these examples.

EXAMPLES

Example 1

Preparation of a hybrid-graft emulsion copolymer of a sulfopolyester grafted with an acid-functional polymer segment consisting of methacrylic acid (MAA), t-butylacrylamide (t-BAM), methyl methacrylate (MMA), and butyl acrylate (BA)

Into a three-neck reaction kettle were placed a sulfopolyester (100 g, EASTMAN AQ®-48 polyester available from Eastman Chemical Company) and water (240 g). The mixture was stirred and purged with nitrogen for thirty minutes while being heated to 65° C. Next, 1% $FeSO_4$—$7H_2O$ (0.5 g) in water (5.0 g), ethylenediaminetetraacetic acid (EDTA) (0.5 g) in water (5.0 g), 90% t-butyl hydroperoxide (0.1 g) in water (5.0 g), and isoascorbic acid (0.1 g) in water (5.0 g) were introduced into the reaction kettle. Next, a mixture of methacrylic acid (40 g), t-butyl acrylamide (20 g), butyl acrylate (30 g), methylmethacrylate (10 g) and 2 ethylhexyl-3 mercaptopropionate (1.0 g) was charged into the reaction kettle along with t-butyl hydroperoxide (0.3 g) in water (50 g) and isoascorbic acid (0.3 g) in water (50 g) over a 60 minute period. The reaction was allowed to stir for an additional 90 minutes with additional t-butyl hydroperoxide (0.2 g) in water (5.0 g) and isoascorbic acid (0.2 g) in water (5.0 g) to produce the desired hybrid-graft emulsion copolymer.

The hybrid-graft emulsion copolymer had weight average molecular weight (Mw) of 78,000 and a Tg of 45° C. Less than 50 ppm residual monomers were present.

Example 2

Neutralization of Hybrid-Graft Emulsion Copolymers

Hybrid-graft emulsion copolymers A, B, C, D having the compositions shown in Table I were prepared in accordance with the procedure of Example 1. Seventy-five percent of the acid groups of each of the resulting resins were neutralized with 2-methyl-2-amino-propanol (AMP). The pH of each copolymer, after neutralization, is shown in Table I.

Example 3

Preparation of a Hybrid Graft Emulsion Copolymer of a Sulfopolyester and Two Acid-functional Polymer Segments by a Sequential Addition of Two Monomer Mixtures Into a three-neck reaction kettle were placed a sulfopolyester (50 g, EASTMAN AQ®-48 polyester available from Eastman Chemical Company), sodium lauryl sulfate (1.0 g), and water (240 g). The mixture was then stirred and purged with nitrogen for thirty minutes while being heated to 70° C. Next, 1% $FeSO_4$—$7H_2O$ (0.2 g) in water (2.0 g), EDTA (0.2 g) in water (2.0 g), 90% t-butyl hydroperoxide (t-BHP) (0.1 g) in water (3.0 g), and isoascorbic acid (0.1 g) in water (3.0 g) were introduced into the reaction kettle. A mixture of methacrylic acid (17.0 g), t-butyl acrylamide (8.0 g), methyl methacrylate (17.0 g), butyl acrylate (8.0 g), and 2-ethylhexyl-3-mercaptopropionate (0.8 g) was then charged into the reaction kettle along with t-butyl hydroperoxide (0.1 g) in water (15 g) and isoascorbic acid (0.1 g) in water (15.0 g) over a 40 minute period. The reaction mixture was allowed to stir an additional 30 minutes followed by charging with a mixture of methacrylic acid (34.0 g), t-butyl acrylamide (16.0 g), butyl acrylate (50.0 g) and 2-ethylhexyl-3-mercaptopropionate (1.5 g) along with 90% t-BHP (0.3 g) in water (15 g) and isoascorbic acid (0.3 g) in water (15.0 g) over an 80 minute period with additional 90% t-BHP (0.1 g) in water (2.0 g) and isoascorbic acid (0.1 g) in water (2.0 g) to produce the desired hybrid-graft copolymer.

Example 4

Evaluation of Hair Care Formulation:

(1) Preparation of 55% Volatile Organic Compound (VOC) aerosol:

After 75% neutralization with AMP following the procedure of Example 2, each hybrid-graft emulsion copolymer of Examples 1 and 2 was aerosolized by the following procedure to give a 55% VOC formulation:

Into a 124 mL vessel, equipped with valve and cup, were placed 21.0 g of a neutralized hybrid-graft emulsion copolymer (7.0 g solid polymer and 14 g water), 20.0 g of Ethanol SDA 40C (anhydrous), 23.3 g of water, and 0.7 g of hexamethyldisiloxane (HMS silicone). After flushing out the air with nitrogen, the valve and cup of the vessel are quickly crimped. A propellant, 35.0 g of dimethyl ether, was then added through a pressurized burette.

(2) Curl Retention:

Eight-inch Remi Blue String European brown hair, available from De Meo Brothers (New York), was divided into two gram swatches, secured at one end, and washed in 10% solution of sodium laureth-2 sulfate (25% active). After rinsing for one minute, the swatches were combed, trimmed to 6 inch lengths, and dried at 120° F.

The swatches were curled after rinsing by rolling it on a ½ inch OD Teflon mandrel, being careful to keep tension as consistent as possible. A plastic clip is used to secure the hair. The curled swatches were dried in an oven for 1 hour at 120° F. After cooling at ambient temperatures (72° F. or less and 50% relative humidity or less), the tresses were carefully unpinned and the curlers removed.

The dry curls were suspended on a hook and an initial curl height reading ($L_o$) was made. The curls were sprayed with a controlled amount of hair spray. For aerosols the curl was suspended from a slowly rotating shaft (20–22 rpm) and sprayed for 4 seconds from a distance of 12 inches. After spraying, the curls were hung an hooks and suspended in a cabinet maintained at 72° F. and 90% relative humidity. The length of the curls were measured at the designated time span.

The percentage curl-retention was calculated according with the following formula:

TABLE I

| Hybrid-Graft Polymer | Eastman AQ 48 (g) | Methyl Methacrylate (g) | n-Butyl Acrylate (g) | Methacrylic Acid (g) | N-tert-Butyl Acrylamide (g) | Ethyl Methacrylate (g) | n-Butyl Methacrylate (g) | pH neutralization |
|---|---|---|---|---|---|---|---|---|
| A | 50 | 5 | 21 | 16 | 8 | | | 7.5 |
| B | 50 | | 21 | 16 | 5 | 8 | | 7.7 |
| C | 50 | | 19 | 16 | 7 | | 8 | 7.4 |
| D | 50 | | 16 | 18 | 9 | 7 | | 7.5 |

$$\% \text{ Curl Retention} = \frac{L - L_t}{L - L_o} \times 100 \qquad (I)$$

where L=length of bunch of hair when extended (base value), $L_o$=length of curl at the beginning of the test, and $L_t$=length of curl after t minutes.

FIG. 1 depicts curl retention at 72° F. and 90% relative humidity (RH) as a function of time for a composition prepared in accordance with Example 1 of the present application, in comparison with three commercial materials.

Figure 2:
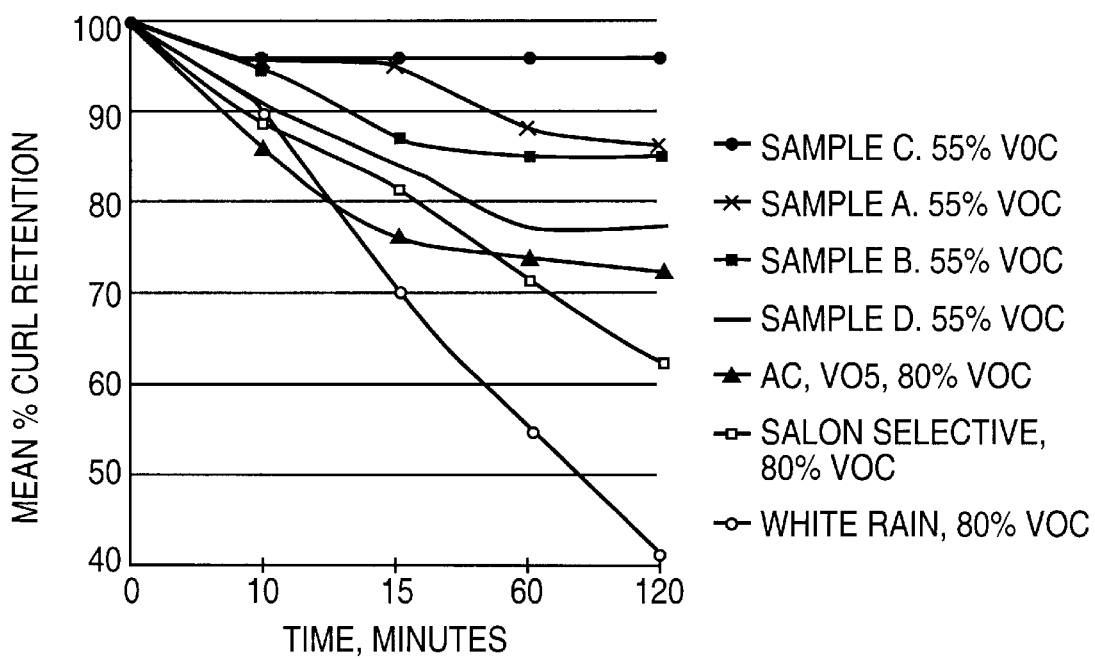
FIG. 2 depicts curl retention properties of neutralized hybrid-graft emulsion polymers (55% VOC) and of commercially available materials (80% VOC) at 72° F. and 90% relative humidity as a function of time.

FIG. 2 and Table II depicts curl retention at 72° F. and 90% relative humidity for Samples A, B, C and D in accordance with the invention at 55% VOC in comparison with commercial products at 80% VOC.

TABLE II

| | % Curl Retention | | | | |
|---|---|---|---|---|---|
| Time, Min. | 0 | 10 | 15 | 60 | 120 |
| White Rain, 80% VOC[1] | 100% | 90 | 70 | 54 | 40 |
| Salon Selective, 80% VOC[2] | 100% | 89 | 81 | 71 | 62 |
| AC, VO5, 80% VOC[3] | 100% | 86 | 76 | 73 | 72 |
| Sample A, 55% VOC | 100% | 96 | 95 | 88 | 86 |
| Sample B, 55% VOC | 100% | 95 | 87 | 85 | 85 |
| Sample C, 55% VOC | 100% | 96 | 96 | 96 | 96 |
| Sample D, 55% VOC | 100% | 91 | 84 | 77 | 77 |

[1]Product of The Gillette Company, Boston, MA.
[2]Product of Helene Curtis, Chicago, IL.
[3]Product of Alberto-Culver Company, Melrose Park, IL.

Numerous modifications and variations of the invention are possible in light of the above teachings. It is therefore to be understood that within the scope of the appended claims, the invention may be practiced otherwise than as specifically described herein.

The claimed invention is:

1. A latex composition for hair care comprising a hybrid-graft copolymer comprising:
   (A) about 2 to about 90 wt %, based on the total hybrid-graft copolymer weight, of a sulfopolyester comprising a condensation polymerization product of:
      (1) about 15 to about 26 mol % dimethyl-5-sodiosulfoisophthalate based on 100 mol % dicarboxylic acid;
      (2) about 60 to about 80 mol % isophthalic acid based on 100 mol % dicarboxylic acid;
      (3) about 10 to about 30 mol % of 1,4-cyclohexanedimethanol based on 100 mol % of diol; and
      (4) about 70 to about 90 mol % diethylene glycol based on 100 mol % of diol; and
   (B) about 10 to about 98 wt %, based on the total hybrid-graft copolymer weight, of an acid-functional polymer segment comprising:
      (1) about 15 to about 50 wt %, based on the total weight of the acid-functional polymer segment, of an acid-functional monomer;
      (2) about 10 to about 80 wt %, based on the total weight of the acid-functional polymer segment, of an ethylenically unsaturated monomer; and
      (3) up to about 40 wt %, based on the total weight of the acid-functional polymer segment, of an amide-functional monomer.

2. A latex composition of claim 1, wherein said sulfopolyester (A) comprises a condensation polymerization product of:
   (1) about 15 to about 26 mol % dimethyl-5-sodiosulfoisophthalate based on 100 mol % dicarboxylic acid;
   (2) about 60 to about 80 mol % isophthalic acid based on 100 mol % dicarboxylic acid;
   (3) about 10 to about 30 mol % of 1,4-cyclohexanedimethanol based on 100 mol % of diol; and
   (4) about 70 to about 90 mol % diethylene glycol based on 100 mol % of diol.

3. A latex composition of claim 1, wherein said sulfopolyester (A) is present in an amount of from about 10 to about 80 wt % and said acid-functional polymer segment is present in an amount of from about 20 to about 90 wt %.

4. A latex composition of claim 1, wherein said sulfopolyester (A) is present in an amount of from about 20 to about 70 wt % and said acid-functional polymer segment is present in an amount of from about 30 to about 80 wt %.

5. A latex composition of claim 1, wherein said acid-functional monomer (1) is present in an amount of from about 20 to about 50 wt %, said ethylenically unsaturated monomer (2) is present in an amount of from about 20 to about 60 wt %, and said amide-functional monomer (3) is present in an amount of from about 4 to about 25 wt %.

6. A latex composition of claim 5, wherein said acid-functional monomer (1) is present in an amount of from about 25 to about 40 wt %.

7. A latex composition of claim 1, wherein said acid-functional monomer (1) is selected from the group consisting of methacrylic acid, itaconic acid, acrylic acid and mixtures thereof; said ethylenically unsaturated monomer (2) is selected from the group consisting of methyl (meth)acrylate, ethyl (meth)acrylate, butyl (meth)acrylate, 2-ethylhexyl (meth)acrylate, 2-hydroxyethyl (meth)acrylate, styrene and mixtures thereof; and said amide-functional monomer (3) is selected from the group consisting of N-t-butyl acrylamide, N-octyl acrylamide, and mixtures thereof.

8. A latex composition of claim 1, wherein said sulfopolyester has a weight average molecular weight (Mw) of from about 4,000 to about 20,000 and a glass transition temperature (Tg) of about 15 to about 60° C.

9. A latex composition of claim 1, wherein said hybrid-graft copolymer has a weight average molecular weight (Mw) of from about 15,000 to about 250,000 and a glass transition temperature (Tg) of from about 15 to about 130° C.

10. A latex composition of claim 9, wherein said hybrid-graft copolymer has a weight average molecular weight (Mw) of from about 20,000 to about 200,000 and a glass transition temperature (Tg) of from about 25 to about 55° C.

11. A latex composition of claim 1, wherein said latex composition is neutralized and has a pH ranging from about 6.0 to about 9.5.

12. A latex composition for hair care comprising a hybrid-graft copolymer comprising:
   (A) about 5 to about 80 wt %, based on the total hybrid-graft copolymer weight, of a sulfopolyester,
   (B) about 15 to about 55 wt %, based on the total hybrid-graft copolymer weight, of a first acid-functional polymer segment, comprising:
      (1) about 15 to about 50 wt %, based on the total amount of the first acid-functional polymer segment, of an acid-functional monomer,
      (2) about 10 to about 80 wt %, based on the total amount of the first acid-functional polymer segment, of an ethylenically unsaturated monomer; and (3) up to about 40 wt %, based on the total amount of the first acid-functional polymer segment, of an amide-functional monomer;

(C) about 5 to about 40 wt %, based on the total hybrid-graft copolymer weight of a second acid-functional polymer segment comprising:
  (1) about 15 to about 50 wt %, based on the total amount of the second acid-functional polymer segment, of an acid-functional monomer,
  (2) about 10 to about 80 wt %, based on the total amount of the second acid-functional polymer segment, of an ethylenically unsaturated monomer; and
  (3) up to about 40 wt %, based on the total of the second acid-functional polymer segment, of an amide-functional monomer;

and wherein said first and second acid-functional polymer segments have different glass transition temperatures.

13. A latex composition of claim 12, wherein said sulfopolyester (A) comprises a condensation polymerization product of:
  (1) about 15 to about 26 mol % dimethyl-5-sodiosulfoisophthalate based on 100 mol % dicarboxylic acid;
  (2) about 60 to about 80 mol % isophthalic acid based on 100 mol % dicarboxylic acid;
  (3) about 10 to about 30 mol % of 1,4-cyclohexanedimethanol based on 100 mol % of diol; and
  (4) about 70 to about 90 mol % diethylene glycol based on 100 mol % of diol.

14. A latex composition of claim 12, wherein said first acid-functional polymer segment has a higher Tg than said second acid-functional polymer segment.

15. A latex composition of claim 12, wherein said first acid-functional polymer segment has a glass transition temperature (Tg) of from about 40 to about 80° C., and said second acid-functional polymer segment has a glass transition temperature (Tg) of from about 20 to about 50° C.

16. A latex composition of claim 12, wherein said latex composition is neutralized and has a pH ranging from about 6.0 to about 9.5.

17. A method for the preparation of a hybrid-graft copolymer composition, comprising the steps of:

(A) forming an aqueous dispersion of a sulfopolyester;

(B) polymerizing in the presence of said aqueous dispersion a first monomer mixture to form a first acid-functional polymer segment, said first monomer mixture comprising:
  (1) about 15 to about 50 wt %, based on the total amount of the first acid-functional polymer segment, of an acid-functional monomer,
  (2) about 10 to about 80 wt %, based on the total amount of the first acid-functional polymer segment, of an ethylenically unsaturated monomer; and
  (3) up to about 40 wt %, based on the total of the first acid-functional polymer segment, of an amide-functional monomer; and (C) polymerizing sequentially a second monomer mixture to form a second acid-functional polymer segment, said second monomer mixture comprising;
  (1) about 15 to about 50 wt %, based on the total amount of the second acid-functional polymer segment, of an acid-functional monomer,
  (2) about 10 to about 80 wt % based on the total amount of the second acid-functional polymer segment, of an ethylenically unsaturated monomer; and
  (3) up to about 40 wt %, based on the total of the second acid-functional polymer segment, of an amide-functional monomer; and (D) optionally, isolating said hybrid graft copolymer composition;

wherein the amount of said sulfopolyester is from about 5 to about 80 wt %, based on the total amount of said hybrid-graft copolymer; the amount of said first acid-functional polymer is from about 15 to about 55 wt %, based on the total amount of said hybrid-graft copolymer; and wherein the amount of said second acid-functional polymer is from about 5 to about 40 wt %, based on the total amount of said hybrid-graft copolymer; and wherein said first and said second acid-functional polymer segments have different glass transition temperatures (Tg).

18. A method of claim 17, wherein said sulfopolyester (A) comprises a condensation polymerization product of:
  (1) about 15 to about 26 mol % dimethyl-5-sodiosulfoisophthalate based on 100 mol % dicarboxylic acid;
  (2) about 60 to about 80 mol % isophthalic acid based on 100 mol % dicarboxylic acid;
  (3) about 10 to about 30 mol % of 1,4-cyclohexanedimethanol based on 100 mol % of diol; and
  (4) about 70 to about 90 mol % diethylene glycol based on 100 mol % of diol.

19. A method of claim 17, wherein said first acid-functional polymer segment has a glass transition temperature (Tg) of from about 40 to about 80° C., and said second acid-functional polymers segment has a glass transition temperature (Tg) of from about 20 to about 50° C.

* * * * *

UNITED STATES PATENT AND TRADEMARK OFFICE
CERTIFICATE OF CORRECTION

PATENT NO. : 6,136,884
DATED : October 24, 2000
INVENTOR(S) : Robert Gow-Sheng Chen et al.

It is certified that error appears in the above-identified patent and that said Letters Patent is hereby corrected as shown below:

Number of Claims,
Change "19" to -- 18 --.

Claims,
Column 15,
Delete lines 65-67.

Column 16,
Delete lines 1-10.

Signed and Sealed this

Thirtieth Day of October, 2001

Attest:

NICHOLAS P. GODICI
Attesting Officer    Acting Director of the United States Patent and Trademark Office